United States Patent [19]
Manley et al.

[11] Patent Number: 5,626,034
[45] Date of Patent: May 6, 1997

[54] MIXED REFRIGERANTS IN ETHYLENE RECOVERY

[76] Inventors: David Manley, 11480 Cedar Grove La.; Hazem Haddad, 825 S. Bishop Rd., both of Rolla, Mo. 65401

[21] Appl. No.: 560,469

[22] Filed: Nov. 17, 1995

[51] Int. Cl.⁶ .................................................. F25J 1/00
[52] U.S. Cl. ........................... 62/623; 62/912; 62/935
[58] Field of Search ........................... 62/623, 912, 935

[56] References Cited

U.S. PATENT DOCUMENTS

| | | |
|---|---|---|
| 2,041,725 | 5/1936 | Podbielniak . |
| 3,364,685 | 1/1968 | Perret . |
| 4,057,972 | 11/1977 | Sarsten ............................. 62/912 |
| 4,274,849 | 6/1981 | Paradowski . |
| 4,504,296 | 3/1985 | Newton et al. . |
| 4,525,185 | 6/1985 | Newton . |
| 4,526,596 | 7/1985 | Baggio et al. ...................... 62/623 |
| 4,545,795 | 10/1985 | Liu et al. . |
| 4,720,185 | 1/1988 | Rowles et al. . |
| 4,726,825 | 2/1988 | Crawford et al. . |
| 4,900,347 | 2/1990 | McCue, Jr. et al. . |
| 5,035,732 | 7/1991 | McCue, Jr. et al. . |
| 5,377,490 | 1/1995 | Howard et al. . |
| 5,379,597 | 1/1995 | Howard et al. ...................... 62/935 |

FOREIGN PATENT DOCUMENTS 1165524  10/1969  United Kingdom .

OTHER PUBLICATIONS

"Mixed Refrigerant Cascade Cycles", Kinard, G.E. et al, Chem. Engrg. Prog., Jan, 1973, vol. 69, No. 1, pp. 56–61.

"Thermodynamic Analysis of Ethylene Plant Distillation Columns", Manley, D.B. et al, 1992 AIChE Spring National Meeting, Section #85—Expansion and Life Extension Techniques in Ethylene Plants, New Orleans, LA, Mar. 31, 1992, pp. 1–8.

*Primary Examiner*—Ronald C. Capossela

[57] ABSTRACT

The present invention is a process of high efficiency rectification zone separation of cracked or other ethylene-containing gas chilled primarily by two closed mixed refrigerant loops and at least part of the dephlegmated overhead gas. The composition of the mixed refrigerants is optimally chosen to obtain an extremely close approach between the process condensation temperatures in the high efficiency rectification zone and the temperature of the chilling streams. An approach of about 3° F. to 8° F. can be achieved for the full condensation curve in the high efficiency rectification zone operating with either ethane or naphtha derived cracked gas. Highly reliable and stable operation is obtained by closed refrigeration loops in the present invention, in addition to reducing high efficiency rectification zone design cost.

12 Claims, 6 Drawing Sheets

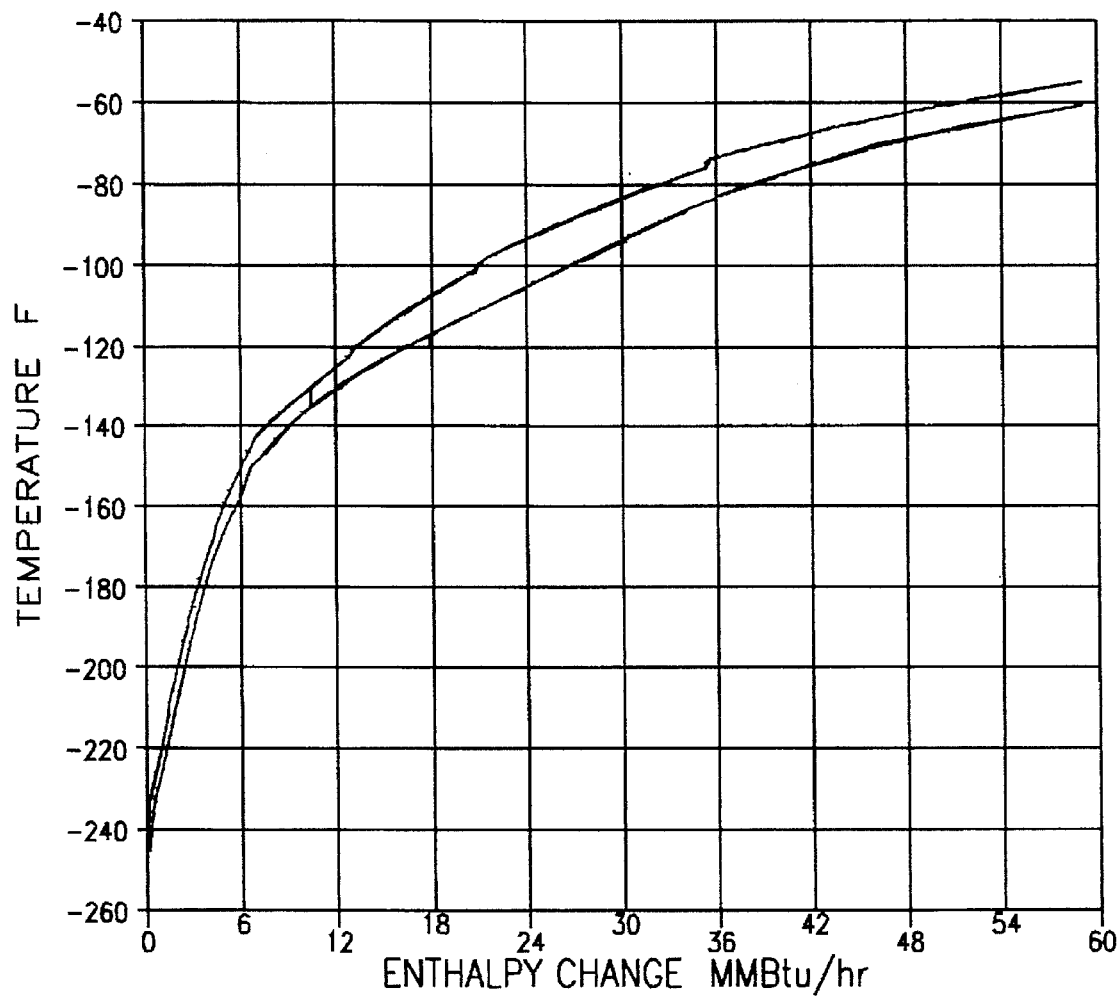

MIXED REFRIGERANTS IN ETHYLENE RECOVERY

BACKGROUND OF THE INVENTION

The present invention relates to the use of closed loop mixed refrigerants in cryogenic separation of hydrocarbons and associated gaseous components.

U.S. Pat. No. 2,041,725 describes a single pressure, multistage, mixed refrigerant system. This early process appears to have served as a model for many later prior art, multistage mixed refrigerant systems. A practice has developed in multicomponent, cascaded refrigerant systems to have sequentially colder partial condensation stages in which the mixed refrigerant is partially condensed and separated at high pressure and then remixed at low pressure. In addition to imposing a significant thermodynamic inefficiency on the system by such separation and re-mixing, proper component distribution in the several loops will be a major operational problem in a highly heat integrated design.

U.S. Pat. No. 3,364,685 is a natural gas liquefaction process using a dual pressure, multistage, mixed refrigerant system in a closed loop. In contrast to U.S. Pat. No. 2,041,725, an intermediate pressure level is added for the mixed refrigerant. It appears that the thermodynamic inefficiency of U.S. Pat. No. 2,041,725 will be partially mitigated by the use of an intermediate pressure level in U.S. Pat. No. 3,364,685, although the additional complexity of distributing the vapor and liquid flows to an appropriate heating load will make the operational problems of U.S. Pat. No. 2,041,725 a greater challenge. The process of correcting imbalanced component ratios in the mixed refrigerant loop of U.S. Pat. No. 3,364,685 will be a confusing task even with careful inspection.

U.S. Pat. No. 4,274,849 is another natural gas liquefaction process with two closed refrigeration loops. The refrigeration loops are integrated so that one loop provides auto-refrigeration with flashed condensate and vapor and simultaneously, in the same pressure shell, indirectly chills the multi-component refrigerant of the second loop. Only the refrigerant of the second loop indirectly chills the natural gas. The second refrigeration loop is further integrated in the following options to chill the process stream. Partially or wholly condensed multi-component refrigerant provides auto-refrigeration with flashed condensate and/or vapor and simultaneously, in the same pressure shell, indirectly chills the process stream. The highly specific heat integration of the process is well understood to involve careful choice of component ratios in both mixed refrigerant loops, natural gas composition, relative pressure levels of the natural gas and the two mixed refrigerant loops. It is not an easy or clear choice to depart from the operation of the system as described in the working examples. Each of many equipment and process design decisions must be balanced against their influence on other equipment and process design decisions to make the system ultimately useful instead of so costly that it is effectively useless.

U.S. Pat. Nos. 4,504,296, 4,525,185 and 4,545,795 are consistent with the above statement in showing the large number of variations that might be made in natural gas liquefaction with two closed refrigeration loops using multi-component refrigerants. Partial condensation and separation of refrigerant streams in auto-refrigeration and in process chilling is not clearly preferred over using the multi-refrigerant streams without such separation. In fact, at the point that the processes require the coldest temperatures for auto-refrigeration or process chilling, most of the processes prefer a partial condensation and separation step to get the benefit of using a vapor stream reduced in heavy components to obtain a lower temperature refrigerant.

U.S. Pat. No. 4,720,293 uses a single closed mixed refrigerant loop for an initial chilling step for a demethanizer in ethylene recovery from cracked gas. The mixed refrigerant is ethane, propane and butane in the molar percentages of 48.3, 18.3 and 33.4. In order to achieve the objects of the patented concept, the ethane product and hydrogen must be combined to provide chilling for the initial chilling step. Such a result has little use in a commercial plant that must recycle ethane to the pyrolysis furnaces.

U.S. Pat. Nos. 4,900,347 and 5,035,732 describe the use of dephlegmators as an integral step in ethylene recovery from cracked gases. The patents share a consistent teaching of the use of single component refrigeration for dephlegmators, either in ethylene and propylene refrigeration loops or in the use of ethane recycle for refrigeration. U.S. Pat. No. 5,377,490 describes the use of a single, open, mixed refrigerant loop to chill two separate process condensation steps. A first chilling step is chilled by a part of mixed refrigerant in the open loop. The chilling duty supplied by the mixed refrigerant is 40% or less. A second condensation step uses a combined stream to chill a dephlegmator. The combined stream comprises the mixed refrigerant from the first chilling step and the net condensate from the dephlegmator. This combined stream is the only chilling stream used in the dephlegmator. The cracked gas is chilled to between −20 to −90 degrees F. before entering the dephlegmator and is the only chilling load in the dephlegmator.

High level ethylene recovery from cracked and other gases is an effort well worth making. The cost of lost ethylene in even very small amounts of ethylene is quite high for a process in continuous operation. However, the components associated with ethylene in cracked gas make such recovery costly in utilities and equipment for cryogenic separation. In addition, cracked gas does not have fixed relative amounts of its several components. Ethane derived cracked gas is very different from propane or naphtha derived cracked gas. Hydrogen, methane, ethylene and ethane vary widely in relation to each other depending on the source of the cracked gas.

Ethylene-propylene cascade refrigeration systems provide the predominant amount of refrigeration required in the ethylene plant. Most of the propylene (high level) refrigeration is utilized at several pressure/temperature levels in the initial feed precooling and fractionation sections of the plant, to cool the feed gas from ambient temperature to about −35° F. and to condense the ethylene refrigerant at about −30° F. Similarly, the ethylene (low level) refrigeration is utilized at several pressure/temperature levels in the cryogenic section of the plant to cool the feed from −35° F. to about −145° F. in order to condense the bulk of the ethylene in the form of liquid feeds to one or more demethanizer columns, and is used in at least one of the demethanizer column overhead condenser(s) at about −100° F. to −145° F. to provide reflux to the column(s). Ethylene is normally not used to provide refrigeration below −150° F. since that would result in sub-atmospheric pressure at the suction of the ethylene compressor. Refrigeration below −150° F. to condense the remaining ethylene from the feed gas is provided primarily by work expansion of hydrogen and methane-containing light gas streams and/or by vaporization of methane refrigerant which has been condensed by ethylene refrigerant. The work expanded gases are normally used as fuel and consist primarily of the overhead vapor from the demethanizer column, mostly methane, and any uncondensed feed gas, mostly hydrogen and methane, which is not processed in a hydrogen recovery section of the ethylene plant or ethylene recovery process. Refrigeration also may be recovered from one or more of the hydrogen-rich and methane-rich streams produced in a hydrogen recovery section.

Cooling and condensation of the feed gas can be accomplished with very high efficiency by dephlegmation in a dephlegmator, which is a rectifying heat exchanger which partially condenses and rectifies the feed gas. Typically a dephlegmator yields a degree of separation equivalent to multiple separation stages, typically 5 to 15 stages. The operation of the dephlegmator is different in kind from other separation devices. The continuous removal of heat from the bottom inlet to the top outlet increases the temperature level at which heat is removed from the rectification stages. The use of single component refrigerants, which provide refrigeration at only a single temperature, are inconsistent with obtaining the continuous heat transfer and separation benefits of dephlegmators.

Alternatively, cooling and condensation of the feed gas is accomplished in a conventional condenser, defined herein as a partial condenser, in which a feed gas is partially condensed to yield a vapor-liquid mixture which is separated into vapor and liquid streams in a simple separator vessel. A single stage of separation is realized in a partial condenser. The advantage to be gained by supplying 5–15 stages of separation in a dephlegmator over an equivalent number or partial condensers and drums is quite clear.

"Mixed Refrigerant Cascade Cycles" (Kinard, G. E. et al, Chemical Engineering Progress, January 1973, Vol. 69, No. 1, pp. 56–61) is an article describing the concept of cascaded, mixed refrigerant loops with reference to LNG. The article points out that significant entropy reduction in the LNG condensation can be obtained by using mixed refrigerants in a process with a single or multiple phase separation in a single mixed refrigerant loop. On page 58, the authors state "Larger cooling curve temperature differences give more irreversible cycles and cause a larger increase in entropy." Although in general entropy reduction is a desirable goal, the complexity of the above prior art processes designed to achieve that goal point out the difficulty in making significant entropy reductions and efficiency improvements through the use of mixed refrigerant cycles.

"Thermodynamic Analysis of Ethylene Plant Distillation Columns" (Manley, D. B. et al, 1992 AIChE Spring National Meeting, Section #85—Expansion and Life Extension Techniques in Ethylene Plants, New Orleans, La., Mar. 31, 1992, pp 1–8) describes "lost work" for each stage of an ethylene plant demethanizer, with separate analysis of momentum, mass transfer and heat transfer. "Lost work" is the difference between actual work done by a specific process and the ideal work available from the operation of any reversible process. On page 7, the authors state that the method of distillation column analysis " ... identifies where distributed distillation and parallel heat transfer/fractionation can be effectively used to improve thermodynamic efficiency and reduce equipment loadings." FIG. 6 shows a comparison of reduced lost work in an improved demethanizer section design. Although general indications by said method of sections in the cooling curve where efficiency improvements might be made, innovation by the skilled person is still generally required to propose process designs which will be effectively analyzed by such methods.

SUMMARY OF THE INVENTION

The present invention is a process of recovery of ethylene from cracked or other ethylene-containing gas chilled primarily by two closed mixed refrigerant loops in a high efficiency rectification step. High efficiency rectification is obtained by use of a number of devices, such as the dephlegmators described above, a distillation column with several intercondensers (typically located at every tray or every other tray), a series plurality of parallel condenser/column devices described in U.S. Pat. No. 4,726,826 or similar devices that countercurrently contact process vapor and liquid streams and have a relatively high degree of multi-level or continuous gradient heat transfer with the process vapor and liquid streams as they pass from one fractionation stage to another. High efficiency rectification devices in the present invention shall hereafter be referred to as "heat integrated rectification sections" or as dephlegmators. Where dephlegmators alone here to be referred to in exclusion of other high efficiency rectification devices, that limitation will be noted at that point in the following description.

Mixed refrigerant composition for the present invention is optimally chosen to obtain an extremely close approach between the process temperatures in the heat integrated rectification section or dephlegmator and the temperature of the chilling streams. An approach of about 3° to 8° F. can be achieved for the full condensation curve in the dephlegmator operating with either ethane or naphtha derived cracked gas. Highly reliable and stable operation is obtained by closed refrigeration loops in the present invention, in addition to reducing dephlegmator design cost.

Condensation of the mixed refrigerant streams is preferably made against the refrigerant whose saturated vapor temperature after vaporization in a heat transfer device is closest to the saturated liquid temperature of the mixed refrigerant to be condensed. Subcooling of a mixed refrigerant stream is preferably done by heat transfer from vaporization of that same mixed refrigerant in the same section of the dephlegmator where the vaporizing mixed refrigerant stream refrigerates the process stream. An alternate embodiment of the present invention uses vaporized mixed refrigerant and process streams to perform additional subcooling of a condensed mixed refrigerant stream.

Thus (1) a higher temperature level mixed refrigerant stream is preferably condensed outside of the dephlegmator against propylene refrigeration and ethane recycle streams (or against other process or refrigeration streams) and is then subcooled in the section of the dephlegmator where the higher level mixed refrigerant vaporizes and (2) a lower temperature level mixed refrigerant is preferably condense in a section of the dephlegmator where the higher level mixed refrigerant vaporizes and is then subcooled in a section of the dephlegmator where the lower temperature level mixed refrigerant vaporizes. Contrary to the strong teaching in the prior art to separate the vapor and liquid portions of the mixed refrigerant for separate heat transfer application, the present invention uses the mixed refrigerants without separation to avoid the thermodynamic inefficiency of separation at high pressure and re-mixing at low pressure in a closed refrigerant loop.

Two mixed refrigerant refrigeration loops have mixed refrigerants with different compositions. A high level mixed refrigerant (HLMR) loop comprises hydrocarbons with an overall molecular weight higher than the overall molecular weight of the low level mixed refrigerant (LLMR) loop. Although the predicted efficiency of the present invention is quite high compared to prior art devices, actual operation of the present invention is anticipated to have a higher efficiency than predicted. The reason for expecting a higher efficiency is that predictive techniques currently generally available do not incorporate a calculation of a truly continuous chilling of non-discrete stages. The stages in a dephlegmator are not physically separated by internals as in a trayed column. Such physical devices are not advantageous in the dephlegmator, as they remove liquid from direct contact with the heat transfer surface. Instead, the irreversibility of rectification is reduced by the provision of mixed refrigerants whose vaporization and chilling temperatures in the dephlegmator generate a generally continuous cooling gradient instead of step changes in temperature resulting from single component refrigerants.

Preferably, the HLMR loop provides chilling for a lower section of the dephlegmator, where the highest temperature range chilling is done for the process stream. Preferably, the LLMR loop provides chilling for an upper section of the dephlegmator, where the coldest temperature range chilling is done. At least a portion of the rectified overhead gas from the dephlegmator, comprising substantially only hydrogen and methane, provides countercurrent chilling to the upper and lower sections of the dephlegmator. The compressed stream for the LLMR loop is preferably condensed in the lower section of the dephlegmator. The compressed stream of the HLMR loop is preferably condensed by refrigerants external to the dephlegmator as described above.

In contrast to the teaching of U.S. Pat. No. 5,377,490, the net rectified liquid obtained as the bottom product of the dephlegmation in the present invention is not used for refrigeration of the preliminary chilling train or dephlegmator. Such condensation is essential for downstream demethanization of the net liquid product to ultimately recover the ethylene from that stream. Open loop refrigeration for dephlegmators make upset recovery very difficult or slow, since the chilling of the dephlegmator will be done by components whose vaporization curve matches a continuous condensation curve for the upset composition, not the desired composition. In a closed refrigeration loop, the desired temperature gradient may be maintained along the length of the chilling surface of the dephlegmator.

The present invention also uses a high purity hydrogen recovery option that coincidentally and preferably increases very low level refrigeration available to the upper section of the dephlegmator. The overhead vapor product of the dephlegmator is first chilled by auto-refrigeration. Partial condensation of the dephlegmator overhead vapor occurs, and the condensation vapor and liquid products are separated in a drum. At this point, hydrogen recovery will preferably operate differently for propane or naphtha derived cracked gases.

For ethane derived cracked gases, the condensation vapor product is high purity (95 mole percent or less) hydrogen. A portion of the condensation vapor product is combined with the condensation liquid product and the mixture is flashed to low pressure. The remaining condensation vapor product and the mixed condensation liquid and vapor product are used to chill their own condensation. Those two streams then first chill the upper and then the lower section of the dephlegmator. The benefit of having separated the hydrogen-rich and methane-rich streams is that the methane-rich stream can be separately flashed to very low pressure to provide streams at −200° F. and below for refrigeration of the dephlegmator independent of the pressure of the hydrogen-rich stream.

For propane or naphtha derived cracked gases, the overhead rectified vapor stream of the dephlegmator will be preferably subjected to a plurality of auto-refrigerated partial condensation and separation stages to recover a methane product stream, a hydrogen product stream and the stream described above as a combination of the hydrogen-rich stream and the methane-rich stream. These streams first auto-refrigerate the partial condensation and separation stages for the overhead vapor stream from the dephlegmator and then chill the upper and lower sections of the dephlegmator. The methane product stream and the combination of the hydrogen-rich stream and the methane-rich stream are reduced in pressure to obtain lower temperature streams.

The hydrogen recovery option produces high purity hydrogen at high pressure while generating very low temperature chilling streams from the methane-rich streams. Re-compression may be required for further processing of the methane-rich streams after they are used for chilling the dephlegmator. However, the optimization of the present invention with the hydrogen recovery option and careful choice of cold (about −30° F.) inlet temperatures for the refrigeration loop compression reduces low temperature energy requirements so substantially that closed loop ethylene refrigeration is eliminated from the ethylene fractionation train. Although the present invention requires two separate compression stages, energy and equipment costs are reduced over prior art designs. The present invention thus accomplishes very high, very efficient recovery of ethylene, optionally producing a high purity hydrogen product. It will be appreciated that the cracked gas pressure at which the present invention will be efficiently used is in the range of 50 to 550 psia, and the temperature, of the cracked gas at the inlet of the dephlegmator is as high as −20° F.

BRIEF DESCRIPTION OF THE DRAWINGS

FIG. 6 is a composite heating and cooling curve for the dephlegmator of the present invention as shown in FIG. 1.

DETAILED DESCRIPTION OF THE INVENTION

Figure 1:
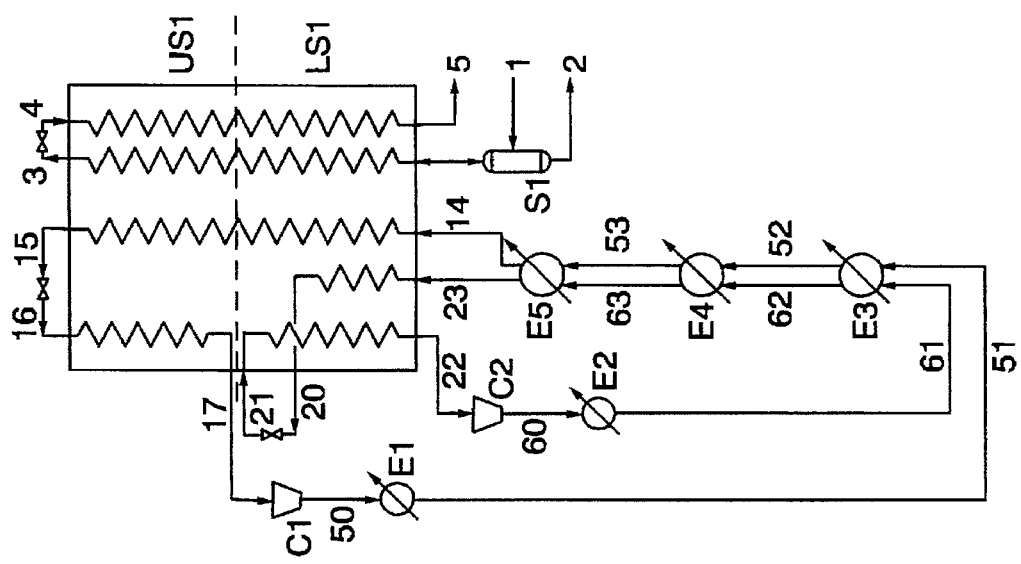
FIG. 1 is a description of the present invention for recovery of ethylene from ethane derived cracked gas using low inlet temperatures for refrigeration loop compression and without using the hydrogen recovery option.

With reference now to FIG. 1, the dephlegmator of the present invention is divided into an upper section US1 and a lower section LS1. Compressors C1 and C2 are generalized representations of single or multi-stage compressors and associated drums, valves and equipment for compressing vaporized mixed refrigerant streams. Exchangers E1 and E2 are preferably cooling water exchangers that cool the mixed refrigerant streams at the outlets of compressors C1 and C2, respectively.

Exchangers E3, E4 and E5 are dual tube bundle exchangers that further cool and condense mixed refrigerant streams 51 and 61 against 20° F. propylene refrigeration, −40° F. propylene refrigeration and −60° F. ethane process furnace recycle respectively. It is known that optimization of heat integration in ethylene plants makes available several process and refrigerant streams for recovery and use of refrigeration utilities. The description of specific refrigerants for exchangers E1, E2, E3, E4 and E5 are not construed to be critical to obtain the objects of the present invention. Other refrigerant or process streams may be used to obtain equal or superior efficiencies in those exchangers depending on the various heat integration designs of a specific ethylene plant.

A high level mixed refrigerant stream (HLMR) is fully condensed in exchanger E4 and/or E5, subcooled in lower section LS1 and is flashed across an external valve. After being flashed across the external valve, the HLMR passes through lower section LS1 before being returned to compressor C2. The condensed and flashed HLMR supplies chilling refrigeration to lower section LS1, preferably introduced to lower section LS1 at about −150° F. to −135° F. and exits lower section LS1 at about −60° F.

A low level mixed refrigerant stream (LLMR) is fully condensed in lower section LS1, is subcooled in upper section LS1 and is then flashed across an external valve. After being flashed across the external valve, the HLMR first passes through to upper section US1 before being returned to compressor C1. The condensed and flashed LLMR supplies chilling refrigeration to upper section US1, preferably introduced to upper section US1 at about −200° F. to −235° F. and exits upper section US1 at about −150° F.

Figure 2:
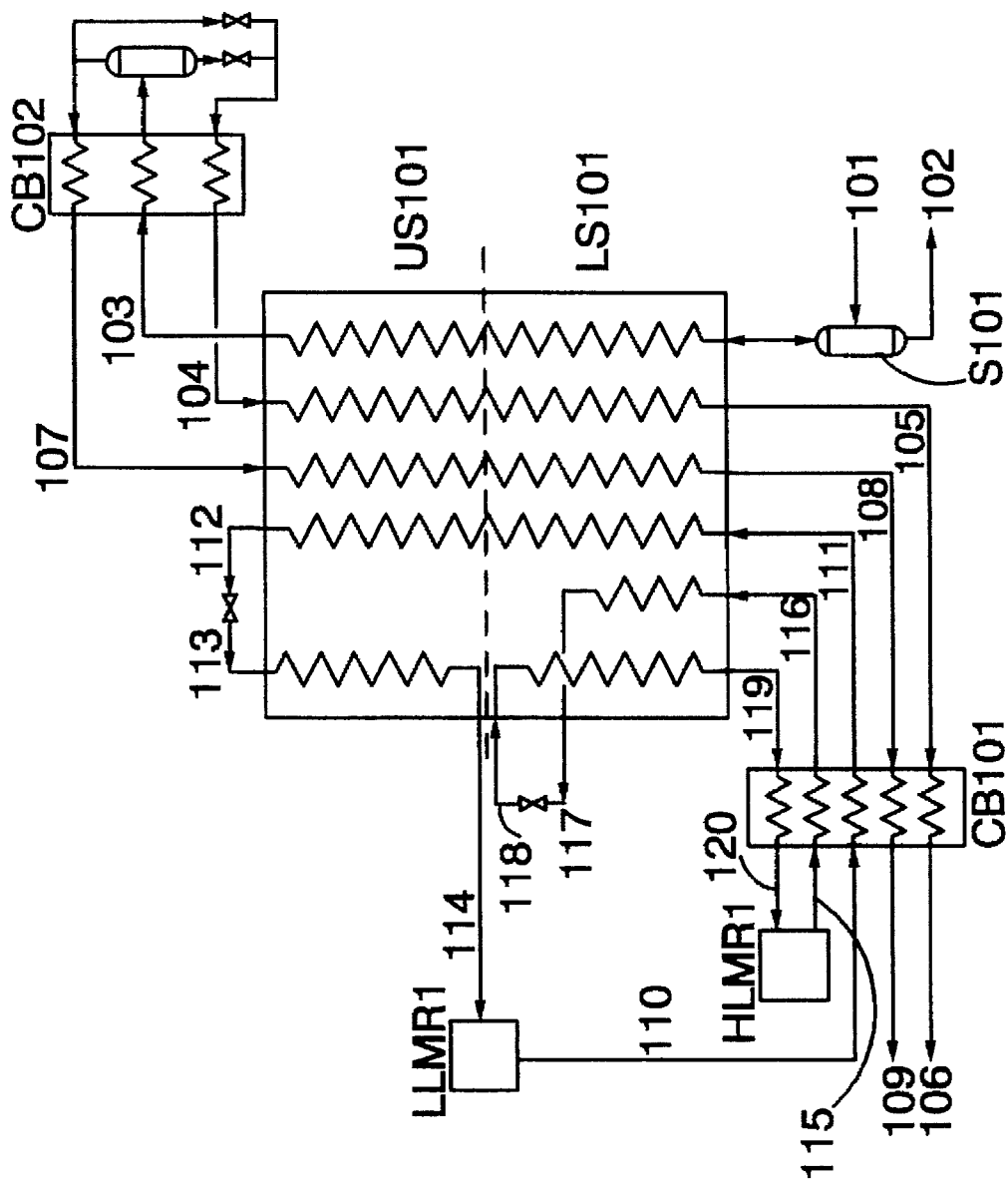
FIG. 2 is a description of the present invention for recovery of ethylene from ethane derived cracked gas using high inlet temperatures for refrigeration loop compression with a hydrogen recovery option.
Figure 3:
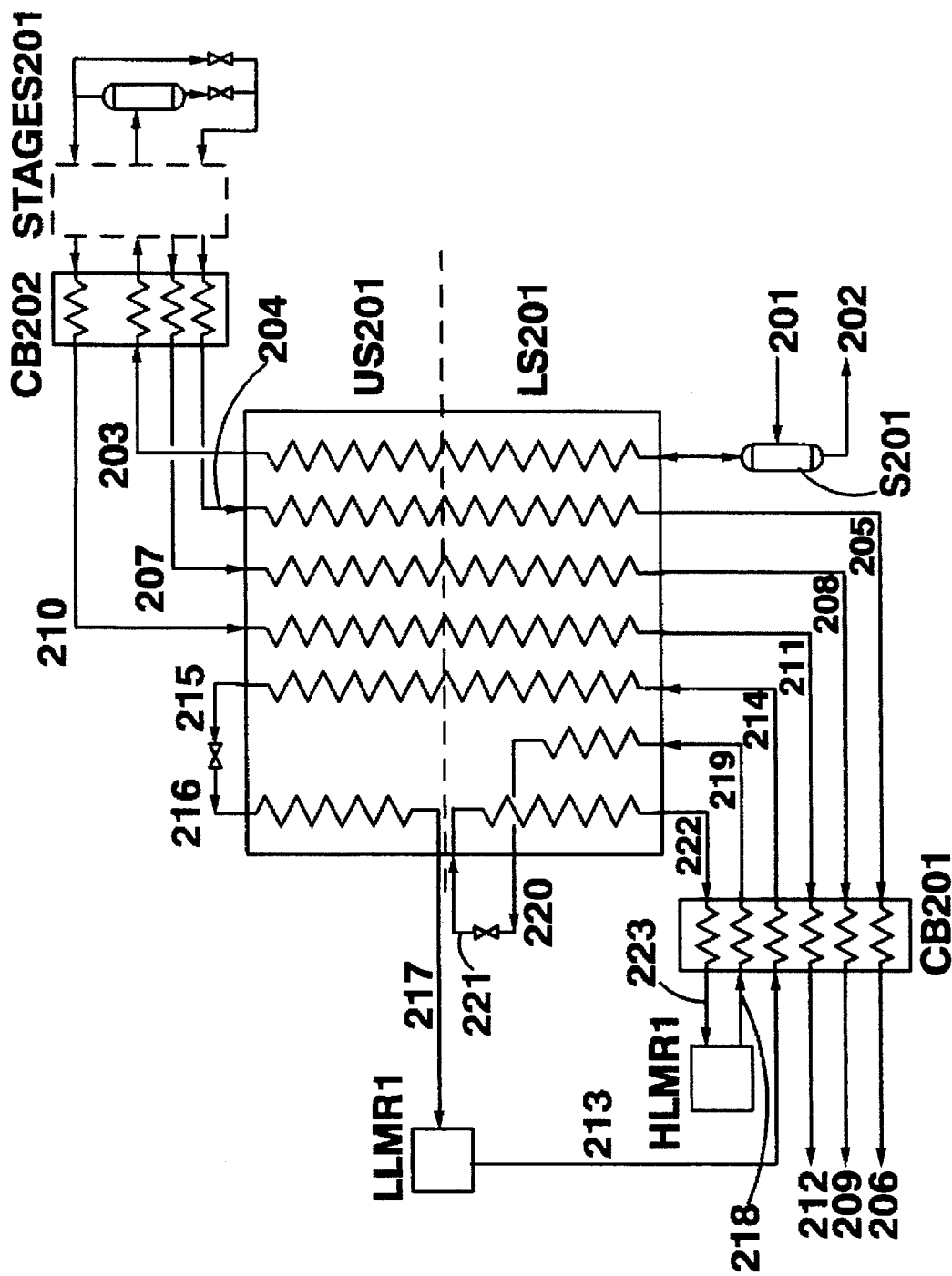
FIG. 3 is a description of the present invention for recovery of ethylene from naphtha derived cracked gas using high inlet temperatures for refrigeration loop compression with a hydrogen recovery option.

In FIG. 1, certain streams and pieces of equipment have been identified. In FIGS. 2 and 3, similar streams and pieces of equipment are used when compared to those of FIG. 1. The following changes relating to the HLMR and LLMR loops are made for the processes shown in FIGS. 2 and 3. In FIGS. 2 and 3, fully condensed HLMR is subcooled and vapor LLMR is cooled by process streams and vaporized HLMR in coldboxes CB101 and CB201. HMLR subcooling in coldboxes CB101 and CB201 reduces the temperature of the condensed refrigerant from about −35° F. to a temperature more consistent with the temperature of the cracked gas as it enters the dephlegmator, thus eliminating the need for the equipment and process step represented by exchanger E5 in FIG. 1. The majority of the condensing duty for HLMR is thus shifted from exchanger E5 (ethane recyle) in the process shown in FIG. 1 to exchanger E4 (−40° F. propylene refrigeration) in the processes shown in FIGS. 2 and 3.

The objective of cooling vapor LLMR in coldboxes CB101 and CB201 is similar to that of subcooling the condensed HLMR therein. It has been found to be advantageous for a somewhat better approach temperature between the cracked gas and the refrigerant streams at their inlets to the dephlegmator than would be possible if exchanger E4 were used without coldboxes CB101 and CB201 in the processes shown in FIGS. 2 and 3. Thermal equilibrium would probably be more difficult to achieve under those circumstances at the cracked gas inlet to the dephlegmator.

The process steps for HLMR achieved in compressor C2 and exchangers E2, E3, and E4 shown in FIG. 1 are shown in generalized form in FIGS. 2 and 3 and there labelled as HLMR1. As discussed above, the equipment and process step of exchanger E5 are eliminated by an innovative recovery of refrigeration duty from vaporized HLMR and process streams.

Similarly, the process steps for LLMR achieved in compressor C1 and exchangers E1, E3 and E4 shown in FIG. 1 are shown in generalized form in FIGS. 2 and 3 and there labelled as LLMR1. As discussed above, the equipment and process step of exchanger E5 are eliminated by innovative recovery of refrigeration duty from vaporized HLMR and process streams.

Again referring to FIG. 1, stream 1 is optionally cracked gas having been chilled in a chilling train typical of prior art demethanizers, or cracked gas that has been fractionated in a deethanizer, an ethane/ethylene or ethylene distributor column. The chilling train comprises partial condensers and separating drums that reduce the temperature of cracked gas to about less than −55° F. Stream 1 passes through drum S1, into the dephlegmator lower section LS1 and then to upper section US1. High efficiency rectification in the dephlegmator of stream 1 produces stream 2, a liquid stream that flows from the bottom outlet of drum S1 typically to a demethanization for separation of ethylene from methane and small amounts of hydrogen. The high efficiency rectification also produces stream 3, a vapor stream from the top outlet of the dephlegmator. Stream 3 is rich in hydrogen and contains very small amounts of ethylene, as well as the majority of the methane contained in stream 1.

Stream 3 is optionally reduced in pressure across a valve or turbine external to the dephlegmator and becomes stream 4. Stream 3 is preferably merely passed from an outlet in the upper section US1 to an inlet in upper section US1 with no pressure reduction. Stream 4 is fed to upper section US1, passes through it to lower section LS1 and out to further processing or chilling utility recovery as stream 5. The operation of the dephlegmator in the present invention for streams 1 and 2 in this FIG. 1 is substantially that of the operation of the dephlegmator shown in FIGS. 2 and 3 for streams 101 and 102 and streams 201 and 202 respectively.

The composition, flow rates and process compositions for the streams shown in FIG. 1 are shown in Table 3. The HLMR for the process shown in FIG. 1 is shown as streams 20, 21, 22 and 23. A preferred composition for the HLMR is substantially ethylene and propylene. The LLMR for the process of FIG. 1 is shown as streams 14, 15, 16 and 17. A preferred composition of the LLMR is substantially nitrogen, methane, ethylene, and ethane with a small amount of propylene.

Mixed refrigerant composition can be optimized with the following considerations. Close attenuation of the heating and cooling curves will depend in part on including in the mixed refrigerants the condensing components of the rectifying process stream. The LLMR streams described in Tables 1, 2, and 3 contain at least about more than 25 mole percent methane, a major component of the rectified overhead vapor stream from the dephlegmator. In contrast, the HMLR streams contain from about 20 to 2 mole percent methane, which is present in the bottom liquid stream from the dephlegmator at less than about 10 mole percent. However, choice of the mixed refrigerant components are not limited to hydrocarbons and may generally be chosen with vaporization and condensation characteristics similar to the components described in Tables 1, 2 and 3.

The HLMR shown in FIG. 1 exits lower section LS1 fully vaporized as stream 22 at 20 psia and −60° F., enters compressor C2 and is compressed to about 150 psia and 150° F. The compressed stream 22 is subsequently cooled in exchangers E2, E3, E4 and E5 to about −55° F. to become stream 23. Stream 23 is fully condensed in exchangers E4 and E5 and is subcooled in lower section LS1 to emerge at −145° F. and become stream 20. Stream 20 is flashed across a valve to become stream 21 at 22 psia at −150° F. Stream 22 is fed into the top portion of lower section LS1 to provide subcooling to stream 23, condensation for stream 14 and the high efficiency rectification of stream 1 in lower section LS1.

The LLMR shown in FIG. 1 exits upper section US1 fully vaporized as stream 17 at 20 psia and −150° F., enters compressor C1 and is compressed to about 275 psia and 170° F. The compressed stream 17 is subsequently cooled in exchangers E1, E3, E4 and E5 to about −55° F. to become stream 14. Stream 14 is condensed in lower section LS1, is subcooled in upper section US1 and emerges at −245° F. to become stream 15. Stream 15 is flashed across a valve to become stream 16 at 22 psia at −250° F. Stream 16 is fed into the top portion of upper section US1 subcooling stream 14 and chilling stream 1.

High efficiency rectification of stream 1 and the operation of the closed mixed refrigerant loops for the HLMR and the LLMR are substantially the same as shown in FIGS. 1, 2 and 3. The above description of FIG. 1 with regard to the high efficiency rectification of stream 1 is applicable to streams 101 and 201 shown in FIGS. 2 and. 3 respectively. Similarly, the operation of the streams 20, 21, 22 and 23 for the HLMR of FIG. 1 is substantially similar to that of streams 115, 116, 117, 118, 119 and 120 shown in FIG. 2, although coldbox CB101 recovers valuable refrigeration utilities from process streams 105 and 108 and vaporized HLMR stream 119 to the mixed refrigerant streams 110 and 115. Also similarly, the operation of the streams 20, 21, 22 and 23 for the HLMR of FIG. 1 is substantially similar to that of streams 218, 219, 220, 221, 222 and 223 shown in FIG. 3, although coldbox CB201 recovers valuable refrigeration utilities from process streams 205, 208 and 211 and vaporized HLMR stream 222 to mixed refrigerant streams 213 and 218.

The operation of the streams 14, 15, 16 and 17 for the LLMR of FIG. 1 is substantially similar to that of streams 110, 111, 112, 113, and 114 shown in FIG. 2, although coldbox CB101 recovers valuable refrigeration utilities from process streams 105 and 108 and vaporized HLMR stream 119 to the condensing mixed refrigerant streams 110 and 115. Similarly, the operation of the streams 14, 15, 16 and 17 for the LLMR of FIG. 1 is substantially similar to that of streams 213, 214, 215, 216 and 217 shown in FIG. 3, although coldbox CB201 recovers valuable refrigeration utilities from process streams 205, 208 and 211 and vaporized HLMR stream 222 to the condensing mixed refrigerant streams 213 and 218.

A critical function of coldboxes of CB101 and CB201 is to integrate with the dephlegmator operation (1) the full condensation of HLMR by propylene refrigerant at about −40°0 F. and (2) the need for a somewhat colder temperature than −35° F. for HLMR and LLMR entering lower sections LS101 and LS201 respectively. The cooling of HLMR and LLMR in coldboxes of CB101 and CB201 is eliminates the need for recycle ethane refrigerant at about −60 F. which is used in the process shown in FIG. 1. Because separator S101 and S201 cracked gas temperature preferably from about −50° to −65° F., HLMR is fully vaporized slightly below that temperature. CB101 and CB201 exchange sensible heat to fill in the thermal gap between the propylene refrigerant temperature and the separator S101 and S201 cracked gas temperature.

Tables 1 and 2 describe the stream compositions, flow rates and process conditions for the process of the present invention shown in FIGS. 2 and 3 respectively. The cracked gas of stream 101 in FIG. 2 is ethane derived. The cracked gas of stream 201 in FIG. 3 is naphtha derived. Inspection of the stream compositions for streams 101 and 201 shows the wide variation in the relative molar amounts of hydrogen, methane, ethylene and ethane. To design the most efficient dephlegmation with the closed refrigeration loops of the present invention, those relative compositions are critical to identifying mixed refrigerant compositions whose vaporization curves most closely match the cooling curves of the dephlegmating cracked gas to be processed. The present invention identifies three sets of such compositions and the pressure levels and compression ratios that will yield the most efficient results for ethane and naphtha cracked gases. Such a disclosure is given in light of the lack of such teaching in the prior art for two independent, closed mixed refrigerant loops in ethylene recovery.

Providing hydrogen recovery can be done with little effect on utilities. Typically, hydrogen recovery is an important process design change requiring extensive investment in equipment and additional refrigeration utilities. Hydrogen recovery according to the present invention may be accomplished with a single core exchanger and autorefrigeration. The process streams from hydrogen recovery can be returned to refrigerate the upper section of the dephlegmator at about −235° F. for ethane derived cracked gas. As shown by comparison of Tables 1 and 3, that is about the same temperature of the dephlegmator overhead vapor stream to be returned to its upper section. However, over 80 mole percent of the hydrogen in the cracked gas is recovered at about 95 mole percent hydrogen. This is an extremely valuable option in light of the current value of recovered hydrogen to hydrocarbon processors.

In addition, providing two closed mixed refrigerant loops instead of one loop permits reduction in overall compression utilities and allows a wider operational flexibility for the present invention. As an example, it will be most efficient that the HMLR be condensed outside the dephlegmator and subcooled in the lower section of the dephlegmator and that LLMR be condensed in the lower section of the dephlegmator and subcooled in the upper section of the dephlegmator. Because a change in furnace feeds is often made gradually, a desired change mixed refrigerant composition can also be gradually made to match the change in dephlegmator cracked gas composition. The components of the mixed refrigerant are readily available in an ethylene plant in a pure form and can be used to quickly or slowly change the mixed refrigerant composition.

FIG. 2 adds a hydrogen recovery option to the process shown in FIG. 1. Stream 103, the rectified vapor overhead from the upper section US 101 of the dephlegmator, is partially condensed by auto-refrigeration and separated in a drum. The methane-rich condensate is flashed across a valve and combined with a flashed portion of the vapor from the partly condensed stream 103 to form stream 104. The rest of the vapor from the partly condensed stream 103 is stream 107, which is the high purity hydrogen stream. Streams 104 and 107 first refrigerate the cooling load in the dephlegmator and then further recover refrigeration utilities to coldbox CB101.

The hydrogen recovery option shown in FIG. 3 for naphtha derived cracked gas uses coldbox CB202 in a similar manner to that shown in FIG. 2 for coldbox CB102, however, a plurality of flashing and/or heat transfer and separation stages, STAGES201, are provided for the liquid product of the partial condensation of stream 203 in coldbox CB202. The additional separation in the hydrogen recovery section of FIG. 3 is generates three product streams instead of two. FIG. 2 shows that streams 104 and 107 are produced with a single separation stage. In FIG. 3, stream 210 (a high purity hydrogen stream), stream 207 (a high purity methane stream) and stream 207 (a stream similar in composition and reduced pressure to stream 104 in FIG. 2) are the three product streams produced from the hydrogen recovery section of the present invention.

Figure 4:
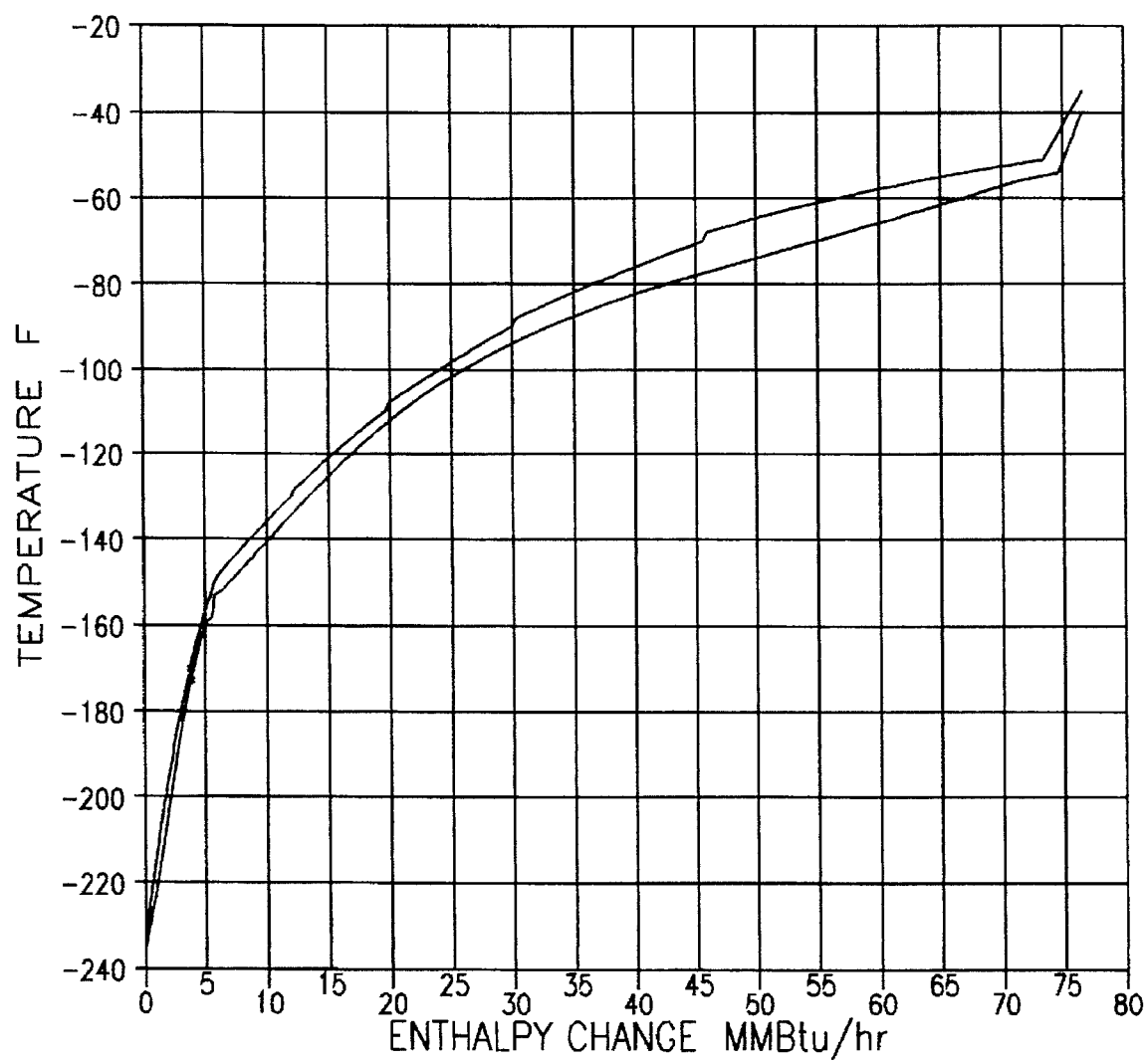
FIG. 4 is a composite heating and cooling curve for the dephlegmator of the present invention as shown in FIG. 2.
Figure 5:
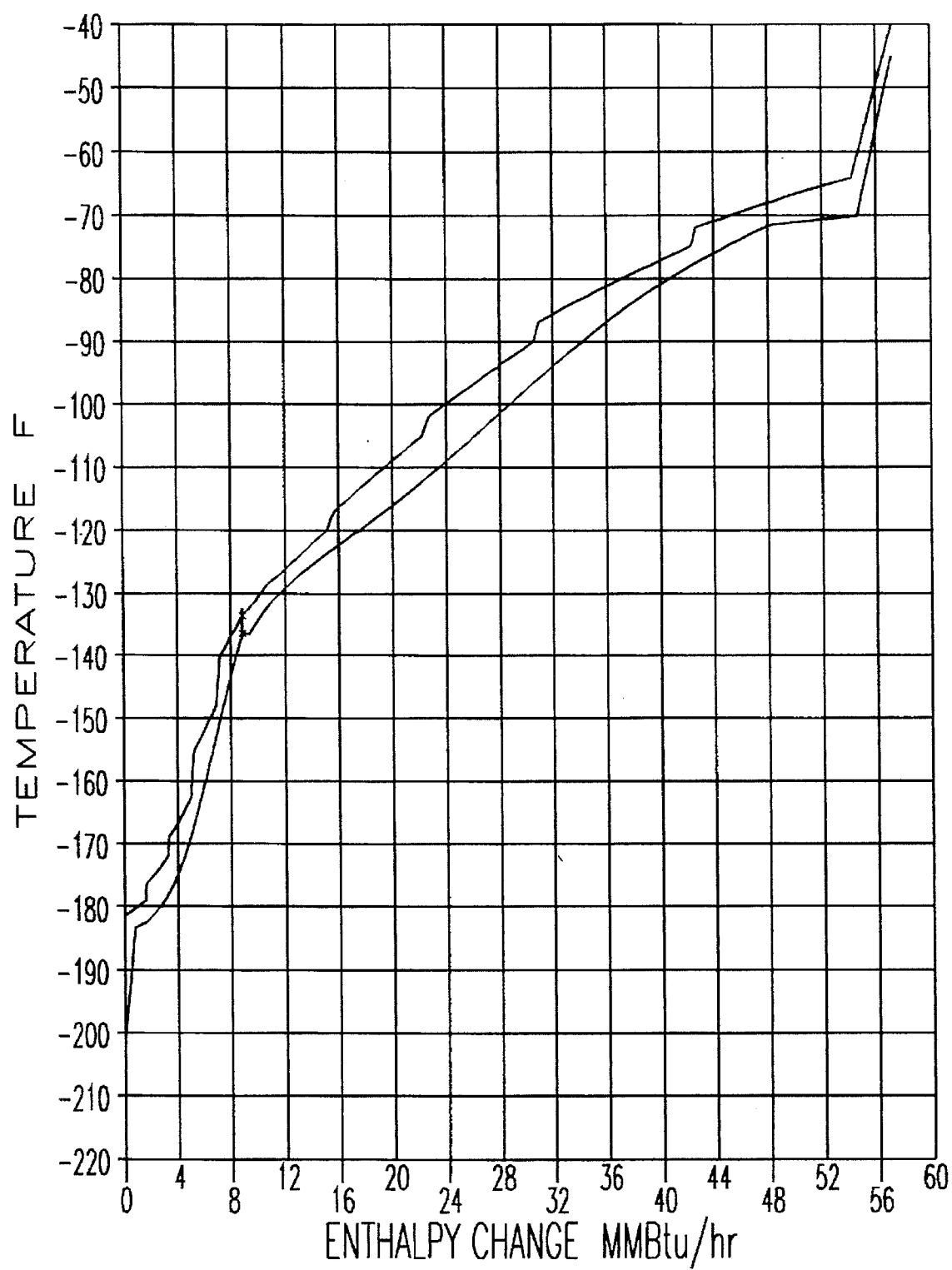
FIG. 5 is a composite heating and cooling curve for the dephlegmator of the present invention as shown in FIG. 3.

FIGS. 4, 5, and 6 represent the composite heating and cooling curves of the dephlegmator of the present invention. FIG. 4 represents the process shown in FIG. 2. FIG. 5 represents the process shown in FIG. 3. FIG. 6 represents the process shown in FIG. 1. The very close matching of utilities to cracked gas dephlegmation is an indication of the careful optimization and hard work of the present inventors to demonstrate the most efficient mode of the present invention for both ethane and naphtha derived cracked gases. The specificity of the examples is not a restriction on the breadth of the teaching of the present invention to use two independent closed, mixed refrigerant loops in the recovery of ethylene at least in the presence of hydrogen and methane. The prior art does not indicate the benefit of using two closed, mixed refrigerant loops in the dephlegmation of hydrocarbons. Although the present invention is directed to the dephlegmation of ethylene in the presence of at least hydrogen and methane, it is applicable to separation of natural gas components where improved efficiency and stability of operation over open, mixed refrigerant loops are used.

It is a benefit of the present invention to eliminate ethylene refrigeration loops of ethylene plants. To obtain that benefit, the C2 splitter, which is the point in the fractionation train other than the demethanizer where ethylene refrigeration may be required, will preferably be heat pumped to complete a substantial portion of its refrigeration utilities, however, an ethylene plant incorporating the present invention will use only cooling water and propylene refrigeration in addition to the two mixed refrigerant loops. Retrofitting an existing plant with the present invention may be possible upon proper re-configuration of an existing ethylene refrigeration compression equipment.

As indicated in the article by Manley et al, lost work in a distillation column, i.e., a demethanizer, is significant at the reboiling and condenser stages. The present invention creates a continous gradient of chilling for recovery of ethylene from cracked gas, reducing the feed stage inefficiencies as well as the inefficiencies relating to single fractionation stage heat transfer. The present invention improves the efficiency of high efficiency rectification devices. As noted above, the term "dephlegmator" has been used herein as a term generally denoting high efficiency rectification devices.

TABLE 1

Ethane Case

| Stream | 101 | 102 | 103 | 104 | 105 | 106 | 107 | 108 | 109 | 110 |
|---|---|---|---|---|---|---|---|---|---|---|
| Vapor frac. | 1.00 | 1.00 | 1.00 | 1.00 | 1.00 | 1.00 | 1.00 | 1.00 | 1.00 | 1.00 |
| Temperature, °F. | −49.2 | −50.9 | −233.0 | −235.8 | −54.0 | −39.8 | −235.8 | −54.0 | −39.8 | −34.8 |
| Pressure, Psia | 302.1 | 302.1 | 300.0 | 24.0 | 22.0 | 20.0 | 296.0 | 294.0 | 292.0 | 206.5 |
| Molar Flow, Lbmole/hr | 15,630 | 10,502 | 5,128 | 536 | 536 | 536 | 4,592 | 4,592 | 4,592 | 547 |
| Mass Flow, MLb/hr | 311.1 | 291.3 | 19.8 | 7.3 | 7.3 | 7.3 | 12.5 | 12.5 | 12.5 | 12.4 |
| Comp. Mole Percent | | | | | | | | | | |
| Hydrogen | 29.00 | 0.71 | 86.94 | 17.85 | 17.85 | 17.85 | 95.00 | 95.00 | 95.00 | 0.00 |
| Nitrogen | 0.00 | 0.00 | 0.00 | 0.00 | 0.00 | 0.00 | 0.00 | 0.00 | 0.00 | 1.04 |
| Methane | 4.99 | 1.10 | 12.96 | 81.20 | 81.20 | 81.20 | 5.00 | 5.00 | 5.00 | 44.37 |
| Ethylene | 65.98 | 98.15 | 0.10 | 0.95 | 0.95 | 0.95 | 0.00 | 0.00 | 0.00 | 54.58 |
| Ethane | 0.03 | 0.04 | 0.00 | 0.00 | 0.00 | 0.00 | 0.00 | 0.00 | 0.00 | 0.00 |
| Propene | 0.00 | 0.00 | 0.00 | 0.00 | 0.00 | 0.00 | 0.00 | 0.00 | 0.00 | 0.00 |

| Stream | 111 | 112 | 113 | 114 | 115 | 116 | 117 | 118 | 119 | 120 |
|---|---|---|---|---|---|---|---|---|---|---|
| Vapor frac. | 1.00 | 0.00 | 0.02 | 1.00 | 0.00 | 0.00 | 0.00 | 0.02 | 1.00 | 1.00 |
| Temperature, °F. | −44.9 | −233.0 | −236.0 | −153.0 | −34.8 | −44.9 | −150.0 | −153.0 | −54.0 | −39.8 |
| Pressure, Psia | 204.5 | 202.5 | 26.5 | 24.5 | 358.2 | 356.2 | 354.2 | 67.2 | 65.2 | 63.2 |
| Molar Flow, Lbmole/hr | 547 | 547 | 547 | 547 | 9,642 | 9,642 | 9,642 | 9,642 | 9,642 | 9,642 |
| Mass Flow, MLb/hr | 12.4 | 12.4 | 12.4 | 12.4 | 277.4 | 277.4 | 277.4 | 277.4 | 277.4 | 277.4 |
| Comp. Mole Percent | | | | | | | | | | |
| Hydrogen | 0.00 | 0.00 | 0.00 | 0.00 | 0.00 | 0.00 | 0.00 | 0.00 | 0.00 | 0.00 |
| Nitrogen | 1.04 | 1.04 | 1.04 | 1.04 | 0.00 | 0.00 | 0.00 | 0.00 | 0.00 | 0.00 |
| Methane | 44.37 | 44.37 | 44.37 | 44.37 | 18.35 | 18.35 | 18.35 | 18.35 | 18.35 | 18.35 |
| Ethylene | 54.58 | 54.58 | 54.58 | 54.58 | 9.07 | 9.07 | 9.07 | 9.07 | 9.07 | 9.07 |
| Ethane | 0.00 | 0.00 | 0.00 | 0.00 | 60.48 | 60.48 | 60.48 | 60.48 | 60.48 | 60.48 |
| Propene | 0.00 | 0.00 | 0.00 | 0.00 | 12.10 | 12.10 | 12.10 | 12.10 | 12.10 | 12.10 |

TABLE 2

Naptha Case

| Stream | 201 | 202 | 203 | 204 | 205 | 206 | 207 | 208 |
|---|---|---|---|---|---|---|---|---|
| Vapor frac. | 1.00 | 1.00 | 1.00 | 1.00 | 1.00 | 1.00 | 1.00 | 1.00 |
| Temperature, °F. | −61.9 | −64.1 | −181.4 | −201.2 | −70.1 | −45.0 | −201.2 | −70.1 |
| Pressure, Psia | 281.3 | 281.3 | 278.6 | 24.0 | 22.0 | 20.0 | 100.0 | 98.0 |
| Molar Flow, Lbmole/hr | 13,134 | 7,726 | 5,408 | 369 | 369 | 369 | 3,762 | 3,762 |
| Mass Flow, MLb/hr | 275.7 | 209.6 | 66.1 | 4.7 | 4.7 | 4.7 | 57.9 | 57.9 |

TABLE 2-continued

Naptha Case

| Comp. Mole Percent | | | | | | | | |
|---|---|---|---|---|---|---|---|---|
| Hydrogen | 11.39 | 0.24 | 27.32 | 23.42 | 23.42 | 23.42 | 4.73 | 4.73 |
| Methane | 34.10 | 7.16 | 72.58 | 76.47 | 76.47 | 76.47 | 95.13 | 95.13 |
| Ethylene | 54.48 | 92.55 | 0.10 | 0.11 | 0.11 | 0.11 | 0.13 | 0.13 |
| Ethane | 0.03 | 0.05 | 0.00 | 0.00 | 0.00 | 0.00 | 0.00 | 0.00 |
| Propene | 0.00 | 0.00 | 0.00 | 0.00 | 0.00 | 0.00 | 0.00 | 0.00 |

| Stream | 209 | 210 | 211 | 212 | 213 | 214 | 215 | 216 |
|---|---|---|---|---|---|---|---|---|
| Vapor frac. | 1.00 | 1.00 | 1.00 | 1.00 | 1.00 | 1.00 | 0.00 | 0.01 |
| Temperature, °F. | −45.0 | −201.2 | −70.1 | −45.0 | −40.0 | −60.9 | −181.4 | −183.3 |
| Pressure, Psia | 96.0 | 274.6 | 272.6 | 270.6 | 401.6 | 399.6 | 397.6 | 147.1 |
| Molar Flow, Lbmole/hr | 3,762 | 1,277 | 1,277 | 1,277 | 1,661 | 1,661 | 1,661 | 1,661 |
| Mass Flow, MLb/hr | 57.9 | 3.5 | 3.5 | 3.5 | 30.0 | 30.0 | 30.0 | 30.0 |
| Comp. Mole Percent | | | | | | | | |
| Hydrogen | 4.73 | 95.00 | 95.00 | 95.00 | 0.00 | 0.00 | 0.00 | 0.00 |
| Methane | 95.13 | 5.00 | 5.00 | 5.00 | 83.10 | 83.10 | 83.10 | 83.10 |
| Ethylene | 0.13 | 0.00 | 0.00 | 0.00 | 16.90 | 16.90 | 16.90 | 16.90 |
| Ethane | 0.00 | 0.00 | 0.00 | 0.00 | 0.00 | 0.00 | 0.00 | 0.00 |
| Propene | 0.00 | 0.00 | 0.00 | 0.00 | 0.00 | 0.00 | 0.00 | 0.00 |

| Stream | 217 | 218 | 219 | 220 | 221 | 222 | 223 |
|---|---|---|---|---|---|---|---|
| Vapor frac. | 1.00 | 0.00 | 0.00 | 0.00 | 0.01 | 1.00 | 1.00 |
| Temperature, °F. | −136.3 | −40.0 | −60.9 | −133.3 | −136.3 | −70.1 | −45.0 |
| Pressure, Psia | 145.1 | 137.3 | 135.3 | 133.3 | 21.0 | 19.0 | 17.0 |
| Molar Flow, Lbmole/hr | 1,661 | 5,695 | 5,695 | 5,695 | 5,695 | 5,695 | 5,695 |
| Mass Flow, MLb/hr | 30.0 | 195.9 | 195.9 | 195.9 | 195.9 | 195.9 | 195.9 |
| Comp. Mole Percent | | | | | | | |
| Hydrogen | 0.00 | 0.00 | 0.00 | 0.00 | 0.00 | 0.00 | 0.00 |
| Methane | 83.10 | 1.61 | 1.61 | 1.61 | 1.61 | 1.61 | 1.61 |
| Ethylene | 16.90 | 51.79 | 51.79 | 51.79 | 51.79 | 51.79 | 51.79 |
| Ethane | 0.00 | 0.00 | 0.00 | 0.00 | 0.00 | 0.00 | 0.00 |
| Propene | 0.00 | 46.61 | 46.61 | 46.61 | 46.61 | 46.61 | 46.61 |

TABLE 3

| Stream | 1 | 2 | 3 | 4 | 5 | 14 | 15 | 16 | 17 | 20 | 21 |
|---|---|---|---|---|---|---|---|---|---|---|---|
| Vapor Frac. | 1 | 0 | 1 | 1 | 1 | 0.97 | 0 | 0.04 | 1 | 0 | 0.02 |
| Temperature, °F. | −55 | −55 | −233 | −233 | −60 | −55 | −245 | −250 | −150 | −145 | −150 |
| Pressure, psia | 310 | 310 | 305 | 305 | 303 | 262 | 258 | 22 | 20 | 133 | 22 |
| Molar Flow, lb-mol/hr | | | | | | | | | | | |
| Mass Flow, Mlb/hr | 293.2 | 273.0 | 20.2 | 20.2 | 20.2 | 15.6 | 15.6 | 15.6 | 15.6 | 216.6 | 216.6 |
| Comp. Mole Percent | | | | | | | | | | | |
| Hydrogen | 29.00 | 0.71 | 86.94 | 86.94 | 86.94 | | | | | | |
| Nitrogen | | | | | | 3.58 | 3.58 | 3.58 | 3.58 | | |
| Methane | 4.99 | 1.10 | 12.96 | 12.96 | 12.96 | 26.75 | 26.75 | 26.75 | 26.75 | 1.97 | 1.97 |
| Ethylene | 65.98 | 98.15 | 0.10 | 0.10 | 0.10 | 62.61 | 62.61 | 62.61 | 62.61 | 35.83 | 35.83 |
| Ethane | 0.03 | 0.04 | | | | 5.53 | 5.53 | 5.53 | 5.53 | | |
| Propene | | | | | | 1.53 | 1.53 | 1.53 | 1.53 | 61.78 | 61.78 |
| n-Butane | | | | | | | | | | 0.23 | 0.23 |
| n-Pentane | | | | | | | | | | 0.19 | 0.19 |

| Stream | 22 | 23 | 50 | 51 | 52 | 53 | 60 | 61 | 62 | 63 |
|---|---|---|---|---|---|---|---|---|---|---|
| Vapor Frac. | 1 | 0 | 1 | 1 | 1 | 1 | 1 | 1 | 0.10 | 0 |
| Temperature, °F. | −60 | −55 | 171 | 100 | 25 | −35 | 149 | 100 | 25 | −35 |
| Pressure, psia | 20 | 135 | 274 | 271 | 268 | 265 | 147 | 144 | 141 | 138 |
| Molar Flow, lb-mol/hr | | | | | | | | | | |
| Mass Flow, Mlb/hr | 216.6 | 216.6 | 15.6 | 15.6 | 15.6 | 15.6 | 216.6 | 216.6 | 216.6 | 216.6 |
| Comp. Mole Percent | | | | | | | | | | |
| Hydrogen | | | | | | | | | | |
| Nitrogen | | | 3.58 | 3.58 | 3.58 | 3.58 | | | | |
| Methane | 1.97 | 197 | 26.75 | 26.75 | 26.75 | 26.75 | 1.97 | 1.97 | 1.97 | 1.97 |
| Ethylene | 35.83 | 35.83 | 62.61 | 62.61 | 62.61 | 62.61 | 35.83 | 35.83 | 35.83 | 35.83 |

TABLE 3-continued

| | | | | | | | | | | |
|---|---|---|---|---|---|---|---|---|---|---|
| Ethane | 5.53 | 5.53 | 5.53 | 5.53 | | | | | | |
| Propene | 61.78 | 61.78 | 1.53 | 1.53 | 1.53 | 1.53 | 61.78 | 61.78 | 61.78 | 61.78 |
| n-Butane | 0.23 | 0.23 | | | | | 0.23 | 0.23 | 0.23 | 0.23 |
| n-Pentane | 0.19 | 0.19 | | | | | 0.19 | 0.19 | 0.19 | 0.19 |

I claim:

1. A process for ethylene recovery comprising:

(a) a first gas substantially comprising hydrogen, methane and ethylene;

(b) passing the first gas through a high efficiency rectification zone first to a lower section and then to an upper section to recover to a first liquid from the lower section substantially all the ethylene in the first gas;

(c) providing heat interchange between the upper section and a first closed, mixed refrigerant loop; and (d) providing heat interchange between the lower section and a second closed, mixed refrigerant loop.

2. The process of claim 1 wherein the mixed refrigerant stream of the first closed, mixed refrigerant loop is condensed in the lower section.

3. The process of claim 2 wherein the mixed refrigerant stream of the second closed, mixed refrigerant loop is subcooled in the lower section and the the mixed refrigerant stream of the first closed, mixed refrigerant loop subcooled in the upper section.

4. The process of claim 1 wherein at no point in the first and second closed, mixed refrigerant loops are their vapor and liquid portions separated by physical separation means.

5. The process of claim 1 wherein a second gas consists of the rectified first gas issuing from the upper section of the high efficiency rectification zone and wherein the second gas in part or entirely is passed countercurrent to the flow of the first gas in the high efficiency rectification zone to recover refrigeration utilities.

6. The process of claim 1 wherein a condensed, flashed mixed refrigerant stream of the first closed, mixed refrigerant loop flows countercurrent to the flow of the first gas in the upper section and a condensed, flashed mixed refrigerant stream of the second closed, mixed refrigerant loop flows countercurrent to the flow of the first gas in the lower section.

7. The process of claim 6 wherein the composition of the mixed refrigerant in the first closed, mixed refrigerant loop comprises substantially methane, ethylene, ethane and propane and the composition of the mixed refrigerant in the second closed, mixed refrigerant loop comprises substantially methane and ethylene.

8. A process for ethylene recovery comprising:

(a) a first gas at about or below −20° F. and at about 50 to 550 psia substantially comprising hydrogen, methane and ethylene;

(b) passing the first gas through a high efficiency rectification zone first to a lower section and then to an upper section to recover to a first liquid from the lower section substantially all the ethylene in the first gas;

(c) providing heat interchange between the upper section and a first closed, mixed refrigerant loop; and (d) providing heat interchange between the lower section and a second closed, mixed refrigerant loop.

9. The process of claim 8 wherein a second gas consists of the rectified first gas issuing from the upper section of the high efficiency rectification zone and wherein the second gas forms a third gas and third liquid after partial condensation and separation, such that the third gas comprises high purity hydrogen at about or below 95 mole percent hydrogen.

10. The process of claim 9 wherein the third liquid and a portion of the third gas are flashed and combined to form a fourth stream, such that the fourth stream and the remaining portion of the third gas first provide refrigeration for the partial condensation and separation of the second gas and second provide refrigeration for the rectification of the first gas.

11. The process of claim 10 wherein, subsequent to providing refrigeration for the rectification of the first gas, the fourth stream, the remaining portion of the third gas and a low pressure gas stream of mixed refrigerant of the first closed, mixed refrigerant loop provide refrigeration for other refrigeration loads in the high efficiency rectification zone.

12. The process of claim 8 wherein:

e) a second gas consists of the rectified first gas issuing from the upper section of the high efficiency rectification zone and wherein the second gas forms a third gas and third liquid after partial condensation and separation, such that the third gas comprises high purity hydrogen at about or below 95 mole percent hydrogen;

f) the third liquid is subsequently partly vaporized and separated to form a fifth gas and fifth liquid, wherein the fifth liquid comprises at about or below 95 mole percent methane;

g) the third gas, fifth gas and fifth liquid first provide refrigeration for the partial condensation and separation of the second gas and second provide refrigeration for the rectification of the first gas; and h) subsequent to providing refrigeration for the rectification of the first gas, the third gas, fifth gas, fifth liquid gas and a low pressure gas stream of mixed refrigerant of the first closed, mixed refrigerant loop provide refrigeration for other refrigeration loads in the high efficiency rectification zone.

* * * * *